United States Patent [19]

Feldhues et al.

[11] Patent Number: 6,121,444
[45] Date of Patent: Sep. 19, 2000

[54] PROCESS FOR PREPARING SUBSTITUTED 4,4'-DIAMINOSTILBENE-2,2'-DISULPHONIC ACID SALTS

[75] Inventors: Ulrich Feldhues, Mount Pleasant, S.C.; Udo Eckstein, Köln, Germany; Uwe Vogt, Monheim, Germany; Rolf Brockmann, Bergisch Gladbach, Germany

[73] Assignee: Bayer Aktiengesellschaft, Leverkusen, Germany

[21] Appl. No.: 09/230,108

[22] PCT Filed: Jul. 31, 1996

[86] PCT No.: PCT/EP96/03357

§ 371 Date: Jan. 22, 1999

§ 102(e) Date: Jan. 22, 1999

[87] PCT Pub. No.: WO98/05653

PCT Pub. Date: Feb. 12, 1998

[51] Int. Cl.[7] .................................................. C07D 251/68
[52] U.S. Cl. ............................................................. 544/193.2
[58] Field of Search ........................................... 544/193.2

[56] References Cited

U.S. PATENT DOCUMENTS

| | | | |
|---|---|---|---|
| 3,025,242 | 3/1962 | Seyler | 544/193.2 |
| 3,532,692 | 10/1970 | Gold et al. | 260/240 |
| 3,925,260 | 12/1975 | Tscharner et al. | 544/193.2 |
| 3,956,283 | 5/1976 | Fleck et al. | 542/461 |
| 4,212,763 | 7/1980 | Fringeli | 544/193.2 |
| 4,466,900 | 8/1984 | Horlacher et al. | 252/301.23 |
| 4,678,852 | 7/1987 | Punzar et al. | 544/193.2 |

FOREIGN PATENT DOCUMENTS

| | | |
|---|---|---|
| 1 250 830 | 9/1967 | Germany . |
| 0154 778 | 4/1982 | Germany . |
| 1593 34 | 3/1983 | Germany . |
| 62-106965 | 5/1987 | Japan . |
| 76705 | 6/1975 | Poland . |
| 62947 | 1/1978 | Romania . |
| 1114021 | 5/1968 | United Kingdom . |
| 1243479 | 8/1968 | United Kingdom . |
| 1174631 | 12/1969 | United Kingdom . |
| 1355218 | 6/1974 | United Kingdom . |

*Primary Examiner*—Mukund J. Shah
*Assistant Examiner*—Venkataraman Balasubramanian
*Attorney, Agent, or Firm*—Joseph C. Gil; Richard E. L. Henderson

[57] ABSTRACT

In the preparation of substituted 4,4'-diaminostilbene-2,2'-disulfonic acid salts a clear increase in the reaction rate may be achieved by carrying out the reaction of the tetrachlorine derivative (III) with the aniline (IV) in the presence of the amine (VI) as acid-absorber.

10 Claims, No Drawings

PROCESS FOR PREPARING SUBSTITUTED 4,4'-DIAMINOSTILBENE-2,2'-DISULPHONIC ACID SALTS

The invention relates to an improved process for the preparation of compounds of the formula

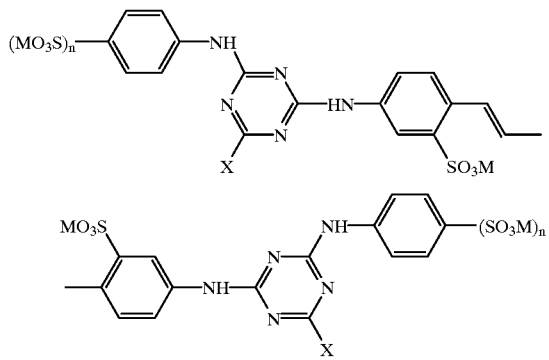

in which n is 0 or 1,

M is an alkali metal ion or an optionally substituted ammonium ion and

X is N-alkylamino or N,N-dialkylamino, and when it is N,N-dialkylamino, the two alkyl radicals which are optionally interrupted by a heteroatom from the series O, N and S, together with the N-atom to which they are bonded may form a saturated 5- or 6-membered heterocycle.

The compounds (I) are important optical brighteners, inter alia for polyamide, cellulose, paper and detergent.

Preferred alkali metal ions are sodium and potassium ions, and a preferred ammonium ion is the triethanolammonium ion.

The alkyl radicals in the combined terms N-alkylamino and N,N-dialkylamino are preferably taken to mean alkyl radicals having up to 4 carbon atoms, which may be interrupted by an O atom and/or may carry a substituent customary in the chemistry of whiteners, such as hydroxyl, cyano, carbamoyl or sulfo.

Examples of saturated 5- and 6-membered heterocycles which can be formed from the two alkyl radicals of the N,N-dialkylamino group and the nitrogen atom to which they are bonded are, for example, pyrrolidine, piperidine, N-methylpiperazine, N-2-hydroxyethylpiperazine and, in particular, morpholine.

Processes for the preparation of compounds (I) from cyanuric chloride, a 4,4'-diaminostilbene-2,2'-disulfonic acid salt of the formula

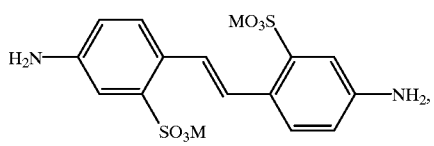
(II)

an aniline of the formula

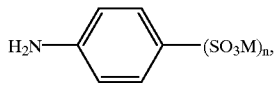
(IV)

in which M and n are as defined above, and an amine XH (VI), X being in each case defined as in (I), are described; DE-AS (German Published Specification) 1 250 830, GB Patent Specification 1 114 021 and 1 174 631, U.S. Pat. No. 3,532,692, PL Patent Specification 76 705, RO Patent Specification 62 947, DD Patent Specification 154 778 and 159 334, CS Patent Specification 228 871 and JP Patent Specification 62/106 965.

Surprisingly, it has now been found that unexpected advantages result when the reaction of the reaction product of cyanuric chloride and (II) with (IV) is carried out in the presence of the amine (VI) as acid-absorber.

The invention thus provides a process for the preparation of compounds of the formula (I) by reaction of cyanuric chloride with a 4,4'-diaminostilbene-2,2'-disulfonic acid salt of the formula (II) in the molar ratio 2:1, subsequent reaction of the resulting compound of the formula

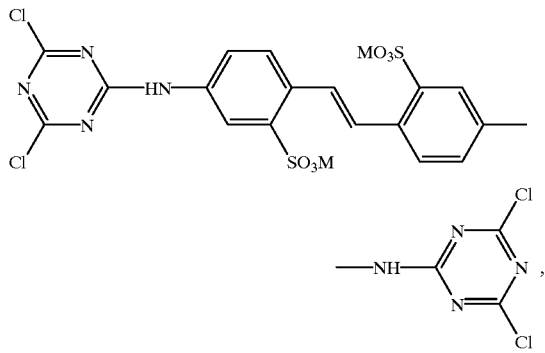
(III)

in which M is as defined above, with 2 equivalents of an aniline of the formula

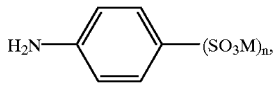
(IV)

in which M and n are as defined above, and subsequent reaction of the resulting compound of the formula

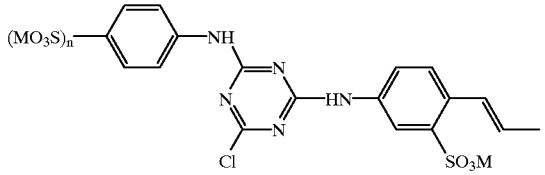
(V)

-continued

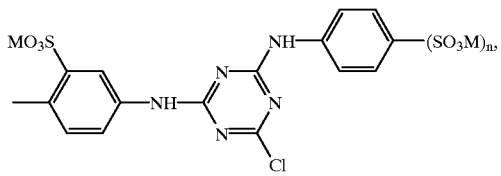

in which M and n are as defined above,
with 2 equivalents of an amine of the general formula XH (VI),
in which X is as defined above, characterized in that (III) is reacted with (IV) in the presence of the amine (VI) as acid-absorber and that, for this purpose, amine (VI) is metered in at a rate such that the pH is maintained in the range from 3.0 to 7.0, preferably in the range from 3.5 to 6.0, in particular in the range from 4.0 to 6.0, and that for the reaction of (V), the amine (VI) is freed from its protonated form by a suitable base.

The process according to the invention leads to a clear increase in the reaction rate, which can be exploited to give a reaction at considerably lower temperatures (i.e. under relatively mild conditions) than previously without conversion losses.

The process according to the invention generally involves, in a first stage, adding a 4,4'-diaminostilbene-2,2'-disulfonic acid dialkali metal salt of the formula (II) in the form of an aqueous solution to an aqueous cyanuric chloride-suspension in the temperature range from 0 to 25° C. and in the pH range from 3.5 to 5.5 in the presence of or with the simultaneous addition of a water-soluble, acid-binding agent for neutralization of the hydrochloric acid liberated. Water-soluble acid-binding agents suitable for this purpose are, for example, alkali metal hydroxides, alkali metal carbonates and alkali metal hydrogencarbonates, such as sodium hydroxide, potassium hydroxide, sodium carbonate, potassium carbonate, sodium hydrogencarbonate and potassium hydrogencarbonate, or triethanolamine. These can be used in solid or liquid form, e.g. gradually via a conveying screw, or advantageously also in the form of their aqueous solutions.

The aqueous cyanuric chloride suspension usually comprises 0.05–2% by weight (based on cyanuric chloride) of wetting surfactant, preferably from the series of alkoxylated fatty alcohols, in particular at least one $C_8$–$C_{14}$-fatty alcohol alkoxylated with from 3 to 10 mol of ethylene oxide and from 0 to 25 mol of propylene oxide, e.g. the polyether of lauryl alcohol and 5 mol of ethylene oxide and/or the polyether of a $C_{10}$-alcohol and 6 mol of ethylene oxide and 8 mol of propylene oxide.

Further, the cyanuric chloride suspension can also comprise from 0.05 to 2.0% by weight (based on cyanuric chloride) of antifoam, about half of which, for example, consists of a mixture of $C_{15}$-alkanesulfamide and ammonium salt of the $C_{15}$-alkanesulfonic acid, and the other half consists of the corresponding $C_{15}$-alkane.

A preferred embodiment of the process according to the invention involves carrying out the addition of the solution of (II), which additionally comprises an amount of a water-soluble acid-binding agent just sufficient to neutralize the hydrochloric acid formed during the reaction, to the aqueous cyanuric chloride suspension under pH control at a set pH from the range 3.5–5.5, preferably 4.0–5.0, at a temperature of from 5 to 20° C., the deviation of the set value generally being no more than −0.5 or +0.3 pH unit. In practice, the end point for the addition of the solution of (II) is reached when, in 10 minutes, less than 0.5% of the solution of (II) is consumed.

The amount of a water-soluble acid-binding agent just sufficient to neutralize the hydrochloric acid formed during the reaction is theoretically 2 equivalents.

The reaction of (M) with (IV) in the presence of the amine (VI) can be carried out in aqueous phase at temperatures of, preferably, from 15 to 75° C., in particular from 20 to 60° C., very particularly preferably from 20 to 40° C. In a particular embodiment, the amine (VI), optionally in the form of a solution, is titrated into the reaction mixture comprising (III) and (IV) under pH control. In the case of such a pH-controlled addition of (VI), a pH chosen from the pH range between 3 and 7 serves as control parameter. If this set value is not reached, (VI) flows into the stirred solution or suspension of (III) until the original value is reached again. This can take place manually or, preferably, automatically with the aid of a titrator. A suitable titrator is, for example, a DULCOMETER® of the type PR F2K2 from Pro Minent.

The deviation from the set pH is generally no more than −0.5 or +0.3 pH units. When (III) has been consumed and therefore no further hydrochloric acid is formed under these conditions, the pH chosen as the set value is established again without falling once more, and the flow stops.

In practice, the end point for the addition of (VI) has already been reached when, in 10 minutes, less than 0.5% of (VI) are consumed.

Particular preference is given to the pH-controlled addition of (VI) at a set pH from the range 4.0 to 6.0, the deviation from this set value generally being no more than −0.5 or +0.3 pH units here as well.

The data of the molar ratio of 2:1 in the case of the reaction of (III) and (IV) and of 2 equivalents (VI) in the case of the reaction with (V) are of course only intended to indicate the theoretical stoichiometry of the reaction. This therefore does not rule out the possibility of, for example, (IV) being used in up to 10% excess or in up to 10% deficit, and, for example, (VI) advantageously also being used in from 5 to 30% excess to complete the reaction.

Preferably, (IV) is allowed to run in as an aqueous solution having a temperature of from 40 to 80° C. and a concentration of over 1.5 mol/l into the suspension of (III).

Preferred amines of the formula (VI) are methylamine, ethylamine, dimethylamine, diethylamine, morpholine, 2-hydroxyethylamine, 2-hydroxypropylamine, in particular di-(2-hydroxyethyl)-amine and di-(2-hydroxypropyl)-amine.

The amine (VI) is protonated by the hydrogen chloride liberated in the reaction of (III) with (IV) with high selectivity and, in this form, does not act as a reactant for (III). The amine (IV) or its aqueous solution may already comprise the amount of (VI) required for neutralization. In this case, it is possible to end the titration when, within 10 minutes, less than 0.5% of the total amount of (VI) theoretically required is consumed.

Following the reaction to give (V), the protonated amine is firstly deprotonated to give the amine (VI) by adding, preferably, in each case 2 equivalents (per amine) of an acid-absorber, and the hydrochloric acid formed during the reaction of (V) with the amine (VI) is absorbed. The reaction of (V) and (VI) can be carried out in a known manner, e.g. by heating the reaction solution for from 2 to 4 hours at temperatures of from 90° C. to the boiling temperature in the presence of an alkali metal hydroxide, a substituted amine or, preferably, an alkali metal carbonate or hydrogencarbonate as acid-absorber. The transesterification of (V) and (VI)

preferably takes place in a pH range below 10.0, the acid-absorber being titrated in under pH control.

The compounds (I) prepared by the process according to the invention can be worked up, for example, by salting out and filtration, or (I) is precipitated out of the warm solution as free acid (M=H) which is sparingly soluble in water, and is filtered off. For the preparation of a storage-stable liquid preparation, the moist crystal cake can then be dissolved in water in a known manner, optionally with the addition of one or more formulating auxiliaries, such as nonionic or anionic surfactants and/or polar organic solubilizers such as polyglycols or urea, and in the case of the free acid, a base is added in an amount such that this is converted back into a readily water-soluble salt. A very simple, inexpensive work-up involves largely desalinating the crude solution of (I) by membrane separation processes under pressure (pressure permeation), concentrating it and converting it directly into the commercially available stable liquid preparation, e.g. in accordance with German Patent Specification 32 34 784 or DE-OS (German Published Specification) 22 04 725.

This rational work-up method can be applied all the more successfully the purer the crude brightener solutions which the process provides, since the byproducts and impurities, with the exception of the low molecular weight fractions, are not discharged with the permeate during pressure permeation, and thus finally remain in the brightener preparation and may impair the efficiency thereof.

The percentages in the examples below are in each case by weight.

EXAMPLE 1

700 ml of water and 10 g of sodium chloride are introduced into a reactor and stirred for 10 min. 1.0 g of a polyether from isodecyl alcohol, 6 mol of ethylene oxide and 8 mol of propylene oxide are then added with stirring, and the mixture is cooled to about 10° C.

100 g of cyanuric chloride (0.542 mol) are then introduced with stirring, and rinsing is carried out with 100 ml of water, and the suspension is stirred until the pH drops to 4.5 by itself.

Using an automatic titrator set at the upper limit value of pH 4.5, an aqueous solution, which is cooled to 10° C. and contains 0.25 mol of 4,4'-diaminostilbene-2,2'-disulfonic acid disodium salt and 0.25 mol of sodium carbonate per liter, is titrated in, the temperature of the reaction mixture being allowed to rise to 18° C.

Theoretically, 1084 ml of solution can be consumed. The end point of the reaction is reached when, within 10 minutes, less than 5 ml are consumed. This is the case after from 2 to 2.5 hours at a consumption of 99% of theory. A readily stirrable pale yellow suspension forms.

The titrator reservoir is changed. The titrator reservoir contains 87.2 g of an 80% strength aqueous diethanolamine solution (0.664 mol). The mixture is then stirred for 30 min at pH 4.5.

500 ml of sodium sulfanilate solution, which comprises 0.528 mol of sodium sulfanilate in these 500 ml, are then allowed to run in over the course of 30 minutes, the temperature in the reactor being increased to 55° C. The mixture is then stirred for 1 hour at 55° C. Up to this point in time, about 74 g of 80% strength aqueous diethanolamine solution (0.56 mol) are metered in via the titrator. At the end of the after-stirring time, the uptake is less than 2 ml in 10 minutes.

The remainder of the aqueous diethanolamine solution is then allowed to run in, and then 402 g of a 15% strength aqueous soda solution (0.569 mol) over the course of 30 minutes.

The mixture is heated to 101° C. over the course of an hour and maintained at this temperature for 2 hours.

This gives 3.1 kg of a crude aqueous solution having a specific extinction of 54 at 350 nm. The crude solution comprises 3.5% (0.11 kg) of sodium chloride and 10% (0.31 kg) of active substance, which essentially corresponds to the compound of the formula

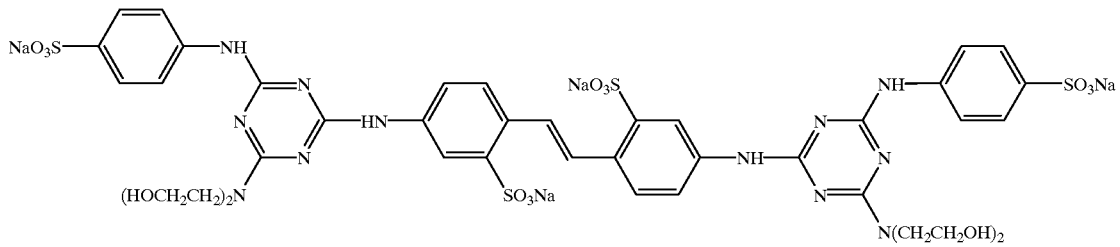

The crude solution is desalinated down to a residual content of 0.5% of sodium chloride by pressure permeation in the manner given in DE-C 32 34 784, Example 2, and then concentrated to a weight of 1.34 kg. This gives an aqueous preparation having a specific extinction of 125 at 350 nm, comprising 23% of active substance and having an electrolyte content of <0.5%.

The same result is achieved when the 500 ml of sodium sulfanilate solution, which comprises 0.528 mol of sodium sulfanilate in these 500 ml, are added in an analogous manner to the above procedure, the temperature in the reactor initially being increased to from 30 to 35° C. and after 90 minutes to 65° C. The mixture is then stirred for 15 minutes at 65° C. and then the above procedure is repeated.

EXAMPLE 2

Example 1 is repeated with the difference that 300 ml of sodium sulfanilate solution of a 60° C. solution comprising 0.528 mol of sodium sulfanilate is used. This gives 2.9 kg of a crude aqueous solution having a specific extinction of 58 at 350 nm. The work-up procedure is as described in Example 1.

EXAMPLE 3

Example 1 is repeated with the difference that instead of di-(2-hydroxyethyl)-amine, an equivalent amount (0.664 mol) of di-(2-hydroxypropyl)-amine are used. The resulting crude aqueous solution (3.1 kg) is desalinated down to a residual content of 0.5% NaCl by pressure permeation and then concentrated until the specific extinction is 142. The resulting 1.17 kg of concentrate are stirred with 130 g of octaethylene glycol homolog mixture (mean molecular weight 400). This gives 1.3 kg of a stable aqueous preparation having a specific extinction of 128 and an electrolyte content of <0.5%.

The brightener conforms to the formula

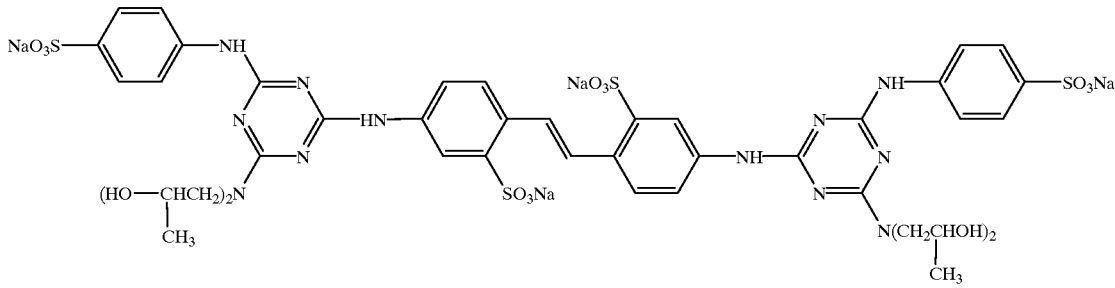

EXAMPLE 4

500 ml of water and 10 g of sodium chloride are introduced into a reactor and stirred for 10 min. 1.0 g of a polyether from isodecyl alcohol, 6 mol of ethylene oxide and 8 mol of propylene oxide are then added with stirring, and the mixture is cooled to about 10° C.

100 g of cyanuric chloride (0.542 mol) are then introduced with stirring, and rinsing is carried out with 100 ml of water, and the suspension is stirred until the pH drops to 4.3 by itself.

Using an automatic titrator set at the upper limit value of pH 4.3, an aqueous solution, which is cooled to 10° C. and contains 0.25 mol of 4,4'-diaminostilbene-2,2'-disulfonic acid disodium salt and 0.25 mol of sodium carbonate per liter, is titrated in, the temperature of the reaction mixture being allowed to rise to 15° C.

Theoretically, 1084 ml of solution can be consumed. The end point of the reaction is reached when, within 10 minutes, less than 5 ml are consumed. This is the case after from 2 to 2.5 hours at a consumption of 99% of theory. A readily stirrable pale yellow suspension forms.

The titrator reservoir is changed. The titrator reservoir contains, in 700 ml, an aqueous solution of 0.61 mol of sodium sulfanilate and 0.64 mol of diethanolamine. The temperature in the reactor is increased to 55° C.

Theoretically, 623 ml of solution should be consumed. The end point of the reaction is reached when, within 10 minutes, less than 3 ml are consumed. This is the case after 1 hour at a consumption of 101% of theory.

17.2 g of a 50% strength aqueous diethanolamine solution are allowed to run in, and then 96 g of sodium hydrogencarbonate (1.14 mol) are added over the course of 30 minutes.

The mixture is heated to 101° C. over the course of one hour and maintained at this temperature for 3 hours.

This gives 2.7 kg of a crude aqueous solution having a specific extinction of 62 at 350 nm. The crude solution comprises 4% (0.11 kg) of sodium chloride and 11.5% (0.31 kg) of active substance, which essentially corresponds to the compound of the formula

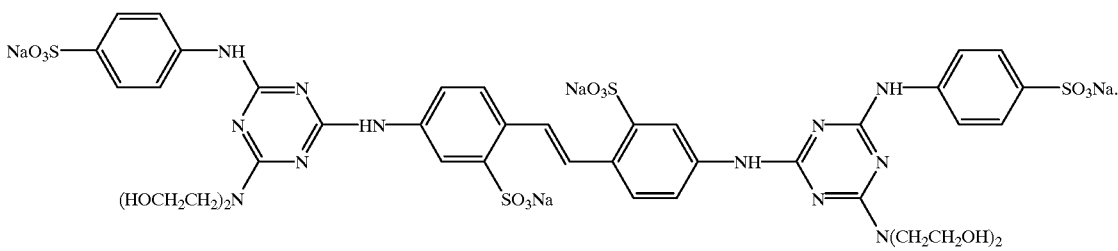

The crude solution is desalinated down to a residual content of 0.5% of sodium chloride by pressure permeation in the manner given in DE-C 32 34 784, Example 2, and then concentrated to a weight of 1.34 kg. This gives an aqueous preparation having a specific extinction of 125 at 350 nm, comprising 23% of active substance and having an electrolyte content of <0.5%.

EXAMPLE 5

700 ml of high-purity water and 10 g of sodium chloride are introduced into a reactor and stirred for 10 min. 1.0 g of a polyether from isodecyl alcohol, 6 mol of ethylene oxide and 8 mol of propylene oxide are then added with stirring, and the mixture is cooled to about 10 ° C.

100 g of cyanuric chloride (0.542 mol) are then introduced with stirring, and rinsing is carried out with 100 ml of high-purity water, and the suspension is stirred until the pH drops to 4.5 by itself.

Using an automatic titrator set at the upper limit value of pH 4.5, an aqueous solution, which is cooled to 10° C. and contains 0.3 mol of 4,4'-diaminostilbene-2,2'-disulfonic acid disodium salt and 0.3 mol of sodium carbonate in 1200 ml, is titrated in, the temperature of the reaction mixture being allowed to rise to 18° C.

Theoretically, 1084 ml of solution can be consumed. The end point of the reaction is reached when, within 10 minutes, less than 5 ml are consumed. This is the case after from 2 to 2.5 hours at a consumption of 99% of theory. A readily stirrable pale yellow suspension forms.

The titrator reservoir is changed. The titrator reservoir contains 87.2 g of an 80% strength aqueous diethanolamine solution (0.664 mol). The mixture is then stirred for 30 min at pH 5.5.

50.2 g of aniline (0.54 mol) are then allowed to run in over the course of 30 minutes, the temperature in the reactor being maintained at 20° C. The mixture is then stirred for 1 hour at 20° C. Up until this point in time, about 74 g of 80% strength aqueous diethanolamine solution (0.56 mol) have been metered in via the titrator. At the end of the after-stirring time, the uptake is less than 2 ml in 10 minutes. At 20° C., 216 g of 10% strength sodium hydroxide solution (0.54 mol) are firstly allowed to run in over the course of 30 min, followed by the remainder of the aqueous diethanolamine solution.

The mixture is heated to 95° C., and the pH is maintained at 7.5 even during the heating-up phase by the titrimetric addition of sodium hydroxide solution (10% strength). The pH and temperature are kept constant for 4 hours.

The mixture is allowed to cool to 85° C., and a pH of 4.2 is set at this temperature by adding hydrochloric acid. The mixture is then stirred for 30 min and allowed to cool to from 50 to 55° C.

The mixture is filtered with suction through a suction filter and carefully washed with water. Drying at 50° C. under reduced pressure gives 245 g of product.

The product corresponds to the compound of the formula

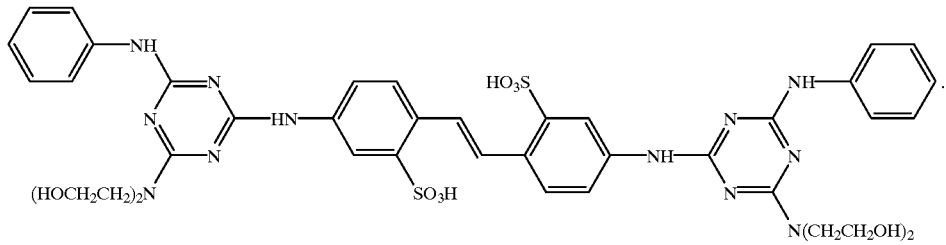

What is claimed is:
1. A process for the preparation of compounds of the formula (I)

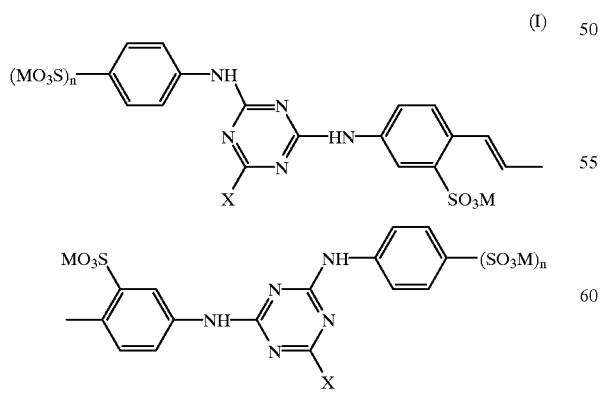

in which
n is 0 or 1,

M is an alkali metal ion or an ammonium ion of an optionally substituted amine, and X is N-alkylamino or N,N-dialkylamino, wherein the alkyl groups can be substituted with hydroxyl, cyano, carbamoyl, or sulfo groups, with the proviso that when X is N,N-dialkylamino, the two alkyl radicals, together with the N-atom to which they are bonded, can form a saturated 5- or 6-membered heterocycle which can be optionally interrupted by a hetero atom from the series O, N, and S, comprising (a) reacting cyanuric chloride with a 4,4'-diaminostilbene-2,2'-disulfonic acid salt of the formula (II)

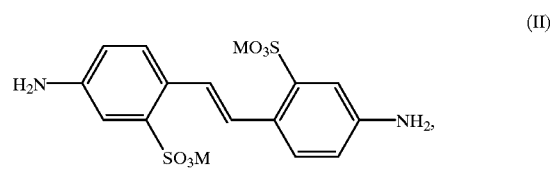

in which M is as defined above, in the molar ratio 2:1 to form a compound of the formula (III)

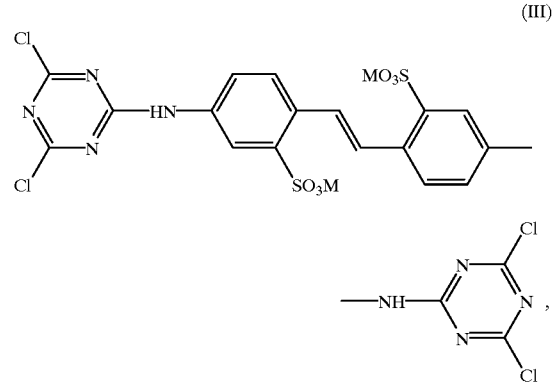

in which M is as defined above, (b) reacting the compound of formula (III) with 2 equivalents of an aniline of the formula (IV)

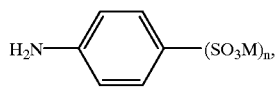

(IV)

in which M and n are as defined above,
to form a compound of the formula (V)

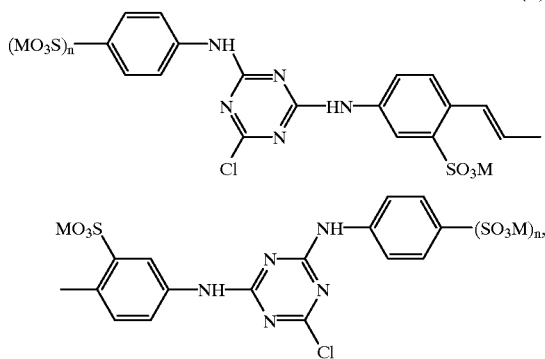

in which M and n are as defined above,
(c) subsequently reacting the compound of formula (V) with 2 equivalents of an amine of the formula XH (VI), in which X is as defined above,
wherein in step (b) the reaction of the compound (III) with the aniline (IV) is carried out in the presence of the amine (VI) as an acid-absorber, said amine (VI) being metered in at a rate that maintains a pH in the range from 3.0 to 7.0, and in step (c) the protonated form of amine (VI) formed in step (b) is freed from its protonated form by adding a base for the reaction with compound (V) the amine (VI) is freed from the protonated form using a base for the reaction with compound (V).

2. The process according to claim 1 wherein the addition of the amine (VI) takes place in the temperature range from 15 to 75° C. at a set pH of from 3.5 to 6.0, the deviation from this set value being no more than from −0.5 to +0.3 pH units.

3. The process according to claim 1 wherein the addition of the amine (VI) takes place in the temperature range from 20 to 60° C. at a set pH of from 4.0 to 6.0, the deviation from this set value being no more than from −0.5 to +0.3 pH units.

4. The process according to claim 1 wherein the reaction of cyanuric chloride with 4,4'-diaminostilbene-2,2'-disulfonic acid salt (II) is carried out by adding an aqueous solution of the 4,4'-diaminostilbene-2,2'-disulfonic acid salt (II) and an amount of a water-soluble acid-binding agent just sufficient to neutralize the hydrochloric acid formed during the reaction to the aqueous cyanuric chloride suspension under pH control at a set pH from the range 3.5 to 5.5 and a temperature from 5 to 20° C.

5. The process according to claim 1 wherein the reaction of cyanuric chloride with the 4,4'-diaminostilbene-2,2'-disulfonic acid salt (II) is carried out using an aqueous solution of the 4,4'-diaminostilbene-2,2'-disulfonic acid salt (II) cooled to from 5 to 15° C.

6. The process according to claim 1 wherein the compound (IV) used is an aqueous solution having a temperature of from 40 to 80° C. and a concentration greater than 1.5 mol/liter.

7. The process for the preparation of a concentrated liquid preparation of a product obtained according to claim 1 wherein the crude solution of the compound (I) is desalinated using a membrane method under pressure and concentrated.

8. The process according to claim 1 wherein X is di-(2-hydroxyethyl)-amino.

9. The process according to claim 1 wherein in step (b) the aniline (IV) is used in up to 10% excess or in up to 10% deficit and the amine (VI) is used in from 5 to 30% excess.

10. The process according to claim 1 wherein the optionally aqueous solution of the compound (IV) contains an amount of the amine (VI) required to neutralize the hydrogen chloride produced during the reaction of the compound (III) with the aniline (IV), said amine (VI) being titrated in until less than 0.5% of the total theoretically required amount of the amine (VI) is consumed within a period of 10 minutes.

\* \* \* \* \*